United States Patent [19]

Satoh et al.

[11] Patent Number: 4,594,243

[45] Date of Patent: Jun. 10, 1986

[54] BASE COMPOSITION FOR MEDICAMENT AND PHARMACEUTICAL COMPOSITION FOR EXTERNAL MEDICATION

[75] Inventors: Susumu Satoh; Ichiro Kobayashi; Yumiko Takakura; Mitsuru Tamada, all of Ibaraki, Japan

[73] Assignee: Nitto Electric Industrial Co., Ltd., Ibaraki, Japan

[21] Appl. No.: 634,479

[22] Filed: Jul. 25, 1984

[51] Int. Cl.$^4$ .................. A61K 31/74; A61K 31/415; A61K 31/21; A61K 31/075; A61K 31/01

[52] U.S. Cl. ...................... 424/78; 514/399; 514/506; 514/715; 514/762; 514/969; 514/970

[58] Field of Search .................. 424/78; 514/399, 506, 514/715, 762, 969, 970

[56] References Cited

U.S. PATENT DOCUMENTS 3,501,571  3/1970  Yen ........................................ 424/78

OTHER PUBLICATIONS

Remington's Phar. Sciences, pp. 1247 and 1252, 1980.

Primary Examiner—Stanley J. Friedman
Assistant Examiner—John W. Rollins
Attorney, Agent, or Firm—Wenderoth, Lind & Ponack

[57] ABSTRACT

A composition capable of promoting the skin permation or percutaneous absorption of a medicament, which comprises at least one adjuvant selected from the group consisting of a saturated hydrocarbon containing 5 to 20 carbon atoms which may be substituted by halogen, an alcohol ester of aliphatic carboxylic acid containing 12 to 18 carbon atoms, an ether, a dimethylpolysiloxane having a viscosity at 25° C. of not more than 6 centistokes and a cyclic polydimethylsiloxane having a viscosity at 25° C. of not more than 6 centistokes, and an imidazolidinone derivative represented by the general formula:

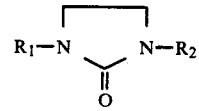

wherein $R_1$ and $R_2$ each are a lower alkyl group; and pharmaceutical composition for external medication.

5 Claims, No Drawings

BASE COMPOSITION FOR MEDICAMENT AND PHARMACEUTICAL COMPOSITION FOR EXTERNAL MEDICATION

TECHNICAL FIELD

This invention relates to a base composition for medicament capable of enhancing percutaneous absorption of the medicament and to a pharmaceutical composition containing the base composition for external medication.

BACKGROUND OF THE INVENTION

Heretofore, medicaments for percutaneous administration were designed for topical actions on the epidermis or its subjacent tissue, such as pasteurization, sterilization, analgesic action, etc.

Recently, however, attempts have been made to administer medicaments having a systemic effect through the epidermis as well as by oral route and injection. Percutaneous administration of medicaments, particularly ones acting systemically is advantageous in that lasting of medicinal efficacies of the medicaments are facilitated; absorption rate of the medicaments is regulated so easily that side effects due to overdosing can be alleviated; the medicaments are so difficult to undergo the metabolism due to first-pass effect by the liver as seen upon oral administration that effective use of them is possible; even such medicaments that cause gastroenteric disorders by oral administration, e.g. indomethacin can be administered safely.

On the other hand, normal skin generally has, because of its effect of protecting the body, the properties of absorbing or permeating medicaments with difficulty. Consequently, even if medicaments (particularly, medicaments designed for systemic action) are administered in the form of ointments, lotions, etc. as usual, they are absorbed in the body with difficulty at least in an amount sufficient to exert medicinal benefits.

In view of the present situations discribed above, the present inventors have investigated intensively and obtained the following findings:

(1) A composition containing at least one compound (hereinafter may be termed generically adjuvant) selected from the group consisting of a saturated hydrocarbon containing 5 to 20 carbon atoms which may be substituted by halogen, an alcohol ester of aliphatic carboxylic acid containing 12 to 18 carbon atoms, an ether, a dimethylpolysiloxane having a viscosity at 25° C. of not more than 6 centistokes and a cyclic polydimethylsiloxane having a viscosity at 25° C. of not more than 6 centistokes; and an imidazolidinone derivative represented by the general formula:

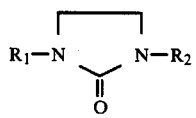

(I)

wherein $R_1$ and $R_2$ each are a lower alkyl enhances percutaneous absorbability of a medicament in the blood.

(2) The above-mentioned composition can be used as a base composition for medicament applicable to the epidermis. This invention has been accomplished on the basis of these findings.

SUMMARY OF THE INVENTION

Accordingly, a primary object of this invention is to provide a base composition for a medicament which enhances the percutaneous absorption of the medicament.

Another object of this invention is to provide a pharmaceutical composition for external application which has a good percutaneous absorbability of a medicament.

A further object of this invention is to provide a method for enhancing the percutaneous absorptivity of a medicament.

That is, this invention consists in:

(1) a base composition for a medicament capable of enhancing the percutaneous absorption of the medicament, which comprises at least one kind of the above adjuvant and an imidazolidinone derivative (I);

(2) a pharmaceutical composition for external application in which a medicament is compounded with the aforesaid base composition; and (3) a method for enhancing the percutaneous absorbability of a medicament characterized in that the medicament is administered to the epidermis in the presence of at least one kind of the adjuvant and an imidazolidinone derivative (I).

DETAILED DISCLOSURE OF THE INVENTION

In the general formula (I), the respective lower alkyls represented by $R_1$ and $R_2$ include those having 1 to 4 carbon atoms such as methyl, ethyl, n-propyl, isopropyl, n-butyl, among which methyl and ethyl are especially preferable (methyl is more preferable). A preferred example of the imidazolidinone derivative (I) is 1,3-dimethyl-2-imidazolidinone.

The saturated hydrocarbon having 5 to 20 carbon atoms which may be substituted by halogen for use in this invention may be straight-chained, branched or cyclic. The straight-chained one includes for example, n-pentane, n-hexane, n-heptane, n-octane, n-nonane, n-decane, n-undecane, n-dodecane, n-tetradecane, n-hexadecane, n-octadecane, n-eicosane, etc., among which preferable are those containing 6 to 16 carbon atoms. The branched one includes for example, 2-methylpentane, 2,3-dimethylhexane, 2,2,4,4,6,8,8-heptamethylnonane, limonene, etc., among which those containing 6 to 12 carbon atoms are preferable. The cyclic one includes ones containing 6 to 12 carbon atoms for example, cyclohexane, cyclododecane, decaline, etc. The halogen as a substituent is chlorine or bromine. The saturated hydrocarbon having halogen substituent includes saturated straight-chained halogenated hydrocarbons containing 8 to 16 carbon atoms, for example, octyl bromide, dodecyl bromide, hexadecyl bromide, dodecyl chloride, etc.

In the alcohol ester of aliphatic carboxylic acid, the carboxylic acid moiety is preferably, aliphatic acids containing 12 to 18 carbon atoms and the alcohol moiety is preferably, monohydroxy alcohols having 1 to 6 carbon atoms, for example, methyl alcohol, ethyl alcohol, n-propyl alcohol, iso-propyl alcohol, n-butyl alcohol, isobutyl alcohol, n-pentyl alcohol, n-hexyl alcohol, etc. Preferable alcohol ester of the carboxylic acid includes for example, hexyl laurate, isopropyl milistate, isopropyl palmitate, butyl stearate, etc.

The ether compound includes one containing 8 to 16 carbon atoms and having one ether linkage in its molecule, for example, dibutyl ether, dihexyl ether, dioctyl ether, methoxydodecane, ethoxydodecane, 1,8-cineole, etc.

Suitable examples of the chain polydimethylsiloxane having a viscosity at 25° C. of not more than 6 centistokes for use in this invention are compounds represented by the general formula:

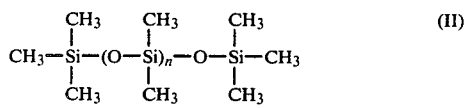

(wherein n is integer of 0 to 6), for example, including hexamethyldisiloxane, decamethyltetrasiloxane, octadecamethyloctasiloxane, dodecamethylpentasiloxane, tetradecamethylhexasiloxane, etc. A suitable cyclic polydimethylsiloxane having a viscosity at 25° C. of not more than 6 centistokes is one having 4- or 5-membered ring, for example including cyclooctamethyltetrasiloxane, cyclodecamethylpentasiloxane, etc.

The base composition for medicament of this invention is prepared by adding an adjuvant to the imidazolidinone derivative (I) and dissolving the both homogeneously, with the amount of the adjuvant being in the range of 1 to 50% by weight, preferably 5 to 30% by weight based on the imidazolidinone derivative (I). Any pharmaceutically acceptable additives may, of course, be compounded in the base composition.

The pharmaceutical composition for external medication according to another aspect of this invention is prepared by adding a medicament to the base composition above and homogeneously mixing or dissolving the mixture.

As a medicament intended for topical actions against diseases of the epidermis or its subjacent tissue, existing external preparations have been useful in their way. In contrast, the medicaments relating to the pharmaceutical composition for external medication of this invention are therefore significant in that they are absorbed in the blood to exert their medicinal efficacies, namely they are aimed at systemic action.

It is preferable that the medicament have a molecular weight of not more than 1000, preferably not more than 700, more preferably not more than 500.

Specific examples of the medicaments are percutaneous medicaments including for example, benzodiazepins (e.g. diazepam, nitrazepam, flunitrazepam, lorazepam, flurazepam, fluidazepam, clonazepam), hypotensive agents (e.g. clonidine), antiinflammatory agents (e.g. indomethacin, diclofenac), thiazide series diuretics (e.g. cyclopenthiazide, trichlorothiazide), arrythmia remedies (e.g. ajmaline, quinidine), central nervous system drugs (e.g. haloperidol, butylscopolamine, chlorpromazine).

The compounding amount of a medicament may be such an amount that is sufficient to exert the medicinal efficacy as desired and may vary and be chosen appropriately depending on the kind of medicament, the body weight and disease conditions of a patient, etc.

The amount of the medicament to be added is usually preferred to be in the range of 0.2 wt.% to 10 wt.% the weight of the pharmaceutical composition for external application. In use, however, the dose of the medicament can be so readily regulated by increasing or decreasing appropriately the area of skin to which the pharmaceutical composition concerned is applied that the compounding amount of the medicament is not always limited to the above-mentioned range.

The pharmaceutical composition for external medication pertaining to the invention, in that state or together with a pharmaceutically acceptable third ingredient, is administered to the epidermis as an external preparation such as ointment, plaster, lotion, adhesive tape preparation, impregnant, gel preparation, etc. The impregnant is, for example, obtained by adsorbing the pharmaceutical composition for external medication concerned or that further compounded with a third ingredient on a suitable adsorptive (gauze, filter paper, porous membrane, etc.), and is usually applied to the epidermis by holding with an adhesive tape thereon. The gel preparation is for example, prapared by gelling the composition with an alcohol gelling agent (e.g. "GELOL D" manufactured by Shin-Nippon Rika Company) followed by extending on a support. As a base agent for the adhesive tape preparation, an acrylic copolymer, polyvinylether, or adhesive mixture of synthetic rubbers is used.

The other external preparations can also be readily prepared by any means well-known per se.

This invention will be hereinafter described more specifically with reference to examples and experimental examples, which are merely illustrative and not limitative of the invention.

EXAMPLES 1-19

Basic Formulation:
(1) Diazepam: 3 g
(2) 1,3-Dimethyl-2-imidazolidinone: 72 g
(3) Adjuvant: 25 g Respective liquid compositions according to the basic formulation above are prepared by the use of respective adjuvants as listed in Table 1 by mixing (3) and (2) and dissolving (1) into the resulting mixture.

COMPARISON EXAMPLE 1

(1) Diazepam: 3 g
(2) 1,3-Dimethyl-2-imidazolidinone: 97 g

The ingredient (1) above is dissolved in (2) to prepare a liquid composition.

COMPARISON EXAMPLE 2

(1) Diazepam: 3 g
(2) Dimethylsulfoxide: 97 g

The above ingredient (1) is dissolved into (2) to prepare a liquid composition.

EXPERIMENTAL EXAMPLE 1

Skin permeation amounts of the medicament in the liquid compositions of Examples 1 to 19 and Comparison Example 1 are measured using the abdominal skins of rats cut out, and results obtained are shown in Table 1.

Measurement Method;

The rat skins each are mounted in a glass cell for permeation, with the outside of them being in contact with the above respective liquid compositions and with the inside of them being in contact with physiological salt solution.

The medicament permeated into the physiological salt solution is extracted with benzene and measured quantatively with spectrophotometer.

TABLE 1

| Example No. | Adjuvant | Medicament Permeation Amount, 0–8 hrs. βg/cm² Average ± Standard Deviation |
|---|---|---|
| 1 | n-hexane | 391 ± 43 |
| 2 | dodecane | 374 ± 51 |
| 3 | hexadecane | 213 ± 38 |
| 4 | isooctane | 277 ± 32 |
| 5 | cyclohexane | 206 ± 29 |
| 6 | cyclododecane | 107 ± 21 |
| 7 | limonene | 199 ± 19 |
| 8 | methyl laurate | 277 ± 26 |
| 9 | hexyl laurate | 191 ± 22 |
| 10 | isopropyl milistate | 211 ± 23 |
| 11 | butyl stearate | 192 ± 17 |
| 12 | octyl bromide | 178 ± 20 |
| 13 | dodecyl bromide | 270 ± 27 |
| 14 | hexadecyl bromide | 142 ± 21 |
| 15 | dodecyl bromide | 271 ± 33 |
| 16 | hexyl ether | 206 ± 19 |
| 17 | 1,8-cineole | 227 ± 24 |
| 18 | hexamethyldisiloxane | 213 ± 30 |
| 19 | cyclooctamethyl-tetrasiloxane | 135 ± 22 |
| Comparison Example 1 | | 71 ± 15 |

EXPERIMENTAL EXAMPLE 2

White rabbits weighing 3.5 kg each are sticked with gauzes of 4 cm² in size impregnated with the respective compositions of Examples 2 and 10 and Comparison Examples 1 and 2 on the skin of the back from which the hair was removed, and bloods of them are taken at time intervals. The medicament is extracted and concentrated in a conventional manner and determined quantitatively with gas chromatography equipped with an electron capture-type detector. Results obtained are shown in Table 2.

TABLE 2

| | Concentration in blood (ng/ml) | | | | |
|---|---|---|---|---|---|
| | 1 hr | 2 hr | 4 hr | 6 hr | 8 hr |
| Example 2 | 45 | 110 | 116 | 75 | 60 |
| Example 10 | 89 | 151 | 170 | 128 | 81 |
| Comparison Example 1 | 30 | 27 | 50 | 57 | 42 |
| Comparison Example 2 | 121 | 140 | 140 | 63 | 50 |

EXAMPLE 20, EXPERIMENTAL EXAMPLE 3

(1) Clonidine-base: 0.8 g
(2) 1,3-Dimethyl-2-imidazolidinone: 75.2 g
(3) Isopropyl milistate: 25 g The above ingredients (2) and (3) are mixed, and (1) is further dissolved in the mixture to prepare a solution.

Wister strain rats each are sticked with a gauze of 0.5 cm² in size impregnated with the above solution on the abdominal skin from which the hair was removed, and their tail arterial blood pressures are measured. Results obtained are shown in Table 3 in comparison with the data of tail arterial blood pressure obtained from the liquid compositions of Comparison Examples 3 and 4 given below:

COMPARISON EXAMPLE 3

(1) Clonidine-base: 0.8 g
(2) 1,3-Dimethyl-2-imidazolidinone: 97.2 g

COMPARISON EXAMPLE 4

(1) Clonidine-base: 0.8 g
(2) Dimethylsulfoxide: 99.2 g

TABLE 3

| | Tail Arterial Blood Pressure, mm Hg | | | | |
|---|---|---|---|---|---|
| | 0 hr | 1 hr | 3 hr | 5 hr | 7 hr |
| Example 20 | 124 | 100 | 87 | 75 | 80 |
| Comparison Example 3 | 130 | 106 | 96 | 80 | 92 |
| Comparison Example 4 | 128 | 107 | 95 | 87 | 99 |
| Non-treatment | 125 | 113 | 122 | 119 | 127 |

EXAMPLE 21

(1) Indomethacin: 1.0 g
(2) 1,3-Dimethyl-2-imidazolidinone: 76.0 g
(3) n-Dodecane: 23.0 g The above ingredients (1), (2) and (3) are mixed and dissolved in a container to prepare a liquid composition.

COMPARISON EXAMPLE 5

(1) Indomethacin: 1 g
(2) 1,3-Dimethyl-2-imidazolidinone: 99 g

The ingredient (1) above is dissolved in (2) to prepare a solution.

COMPARISON EXAMPLE 6

(1) "HIVISWAKO 104"® by Wako Jyunyaku K.K.: 1.0 g
(2) Indomethacin: 1.0 g
(3) Propylene glycol: 12.0 g
(4) Ethyl alcohol: 30 g
(5) Diisopropyl adipate: 2.0 g
(6) Diisopropanolamine: 1.1 g
(7) Purified water: An amount sufficient to bring the total weight to 100 g (A) The ingredient (1) above is swelled in 20 g of water.
(B) The ingredient (2) above is dissolved in (3), (4), (5).
(C) (B) is added to (A) to stir the mixture until it is completely hydrated.
(D) The above ingredient (6) is dissolved in 10 g of water, the resulting solution is added to (C), and the remaining water is added and the mixture obtained is stirred until it becomes homogeneous.

EXPERIMENTAL EXAMPLE 4

Permeation of Indomethacin through the Skins of Rats

Wister-strain male rats weighing 200 g are removed the hair on the abdominal skins with a hair-clipper and an electric razor (Brown Co.). Then, the skins are peeled off, mounted in a glass cell for permeation of medicament, and coated thereon with the above compositions of Example 21 and Comparison Examples 5 and 6 in an amount of 150 mg/1 cm² of skin. Permeation amounts of indomethacin through the skins are measured and results obtained are shown in Table 4.

TABLE 4

| | Indomethacin μg/cm² | | | |
|---|---|---|---|---|
| | 2 hr | 4 hr | 6 hr | 8 hr |
| Example 21 | 14.5 | 63.3 | 140.7 | 211.2 |
| Comparison Example 5 | 3.2 | 22.2 | 46.5 | 81.0 |
| Comparison Example 6 | 0.9 | 4.2 | 13.4 | 24.0 |

We claim:

1. A base composition for a medicament, which base composition is capable of enhancing the percuteneous absorption of the medicament comprising: an effective amount of at least one adjuvant selected from the group consisting of a saturated hydrocarbon containing 5 to 20 carbon atoms which may be substituted by halogen, an alcohol ester of alilphatic carboxylic acid containing 12 to 18 carbon atoms, an ether containing 8 to 16 carbon atoms, a dimethylpolysiloxane having a viscosity of 25° C. of not more than 6 centistokes and a cyclic polydimethylsiloxane having a viscosity at 25° C. of not more than 6 centistokes; and an effective amount of an imidazolidinone derivative represented by the general formula:

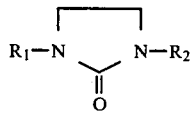

wherein $R_1$ and $R_2$ each are a lower alkyl group.

2. A base composition for a medicament as claimed in claim 1, wherein said imidazolidinone derivative is 1,3-dimethyl-2-imidazolidinone.

3. A base composition for a medicament as claimed in claim 1, wherein said adjuvant is a saturated hydrocarbon containing 6 to 16 carbon atoms which may be substituted by halogen, an ester of an aliphatic carboxylic acid containing 12 to 18 carbon atoms and an alcohol containing 1 to 6 carbon atoms, an ether containing 8 to 16 carbon atoms and having one ether linkage, or a chain polydimethylsiloxane represented by the general formula:

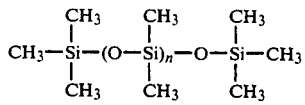

wherein n is an integer of 0 to 6, or a 4- or 5-membered ring polydimethylsiloxane having a viscosity at 25° C. of not more than 6 centistokes.

4. A base composition for a medicament as claimed in claim 1, wherein compounding amount of the adjuvant is in the range of 1 to 50% by weight based on the imidazolidinone derivative.

5. A base composition for a medicament as claimed in claim 1, wherein said adjuvant is dodecane, isopropyl milistate, butyl stearate, dodecyl bromide, 1,8-cineole, hexamethyldisiloxane or cyclooctamethyltetrasiloxane.

* * * * *